US010881127B1

(12) United States Patent
Mun

(10) Patent No.: US 10,881,127 B1
(45) Date of Patent: Jan. 5, 2021

(54) MANUFACTURING METHOD OF WATER-SOLUBILIZED SOLUTION OF MASTIC RESIN

(71) Applicant: VENN SKINCARE, INC., Los Angeles, CA (US)

(72) Inventor: Jae-Choel Mun, Seoul (KR)

(73) Assignee: VINN SKINCARE, INC., Los Angeles, CA (US)

( * ) Notice: Subject to any disclaimer, the term of this patent is extended or adjusted under 35 U.S.C. 154(b) by 0 days.

(21) Appl. No.: 16/653,208

(22) Filed: Oct. 15, 2019

(51) Int. Cl.
  *A23L 33/105* (2016.01)
  *A23L 2/52* (2006.01)
  *B01D 11/02* (2006.01)
  *A61K 36/22* (2006.01)

(52) U.S. Cl.
  CPC ............. *A23L 33/105* (2016.08); *A23L 2/52* (2013.01); *A61K 36/22* (2013.01); *B01D 11/02* (2013.01)

(58) Field of Classification Search
  CPC .. A61K 36/22; A61K 2800/80; A61K 8/0258; A61K 8/553; A61K 8/92; A61K 8/025; A61K 8/34; A61K 8/602; A61Q 19/00; F16L 37/0885; F16L 37/0987; F16L 37/144
  See application file for complete search history.

(56) References Cited

FOREIGN PATENT DOCUMENTS

KR   10-2018-0055331 A   0/2018
KR      10-1311011 B1   9/2013

OTHER PUBLICATIONS

Paraschos S, et al "In vitro and in vivo Activities of Chios Mastic Gum Extracts and Constituents against Helicobacter pylori" Antimicrob Agents Chemother, Feb. 2007 (ePub Nov. 20, 2006), 51(2), 551-559; doi:10.1128/AAC.00642-06. (Year: 2006).*

Roaches S. et al., In Vitro and In Vivo Activities of Chios Mastic Gum Extracts and Constituents against Helicobacter pylori, Antimicrobial Agents and Chemotherapy, Feb. 2007, p. 551-559, vol. 51, No. 2, published by American Society for Microbiology.

Takahashi K, et al., A Pilot Study on Antiplaque Effects of Mastic Chewing Gum in the Oral Cavity, J. Periodontol. pp. 501-505, Apr. 2003. vol. 74, No. 4.

* cited by examiner

*Primary Examiner* — Aaron J Kosar

(57) ABSTRACT

The present invention relates to a method of manufacturing a water-solubilized solution of mastic gum using a novel solvent system. The water-solubilized solution contains no organic solvent such as ethanol. With the new solvent system, a water-solubilized solution of mastic gum can be prepared with no organic solvents such as ethanol, but with a high amount of mastic gum dissolved therein.

5 Claims, 12 Drawing Sheets dissolving mastic gum in ethanol to prepare a first solution(S110)

mixing polyol and purified water to prepare a second solution(S120)

mixing the first solution and the second solution to prepare a third solution(S130)

cooling down the third solution and filtering the third solution to remove insoluble polymer resin(S140)

removing alcohol from the filtered third solution(S150)

FIG. 1

MANUFACTURING METHOD OF WATER-SOLUBILIZED SOLUTION OF MASTIC RESIN

TECHNICAL FIELD

The present invention is related to a solubilization method of water-insoluble mastic gum by applying novel solvent system without organic solvent such as ethanol in the final product.

BACKGROUND OF INVENTION

Mastic is a natural extract obtained from a mastic tree that is grown only on the Greek island of Chios since about 5,000 years ago. Mastic has been widely used in the West since the fifth century B.C.

Mastic resin or mastic gum (hereinafter, referred to as "mastic gum") is an air-dried aromatic resin exudate of Mastic tree (Pistacia lentiscus L). Mastic trees are evergreen shrubs native to the Mediterranean region. Only the Chia varieties, which are cultivated exclusively in the southern part of Greece Chios Island, are known as producing pure, unique and superlative mastic gums.

Currently, mastic gum which is grown in the Greek island of Chios is sold worldwide exclusively through the Chios Gum Mastic Growers Association. Since it is obtained only from mastic trees grown in the south of Chios, its production volume is limited. No natural substances or additives are added through the whole process of its production process.

Mastic gum, together with propolis and xylitol, is known as one of top three natural antibiotics. Mastic gums were used as incense in ancient Egypt and used to embalm the dead. Traditionally, they are known as antioxidants, killing agents, and cures for gastric ulcers, high cholesterol, diabetes, hypertension, etc.

Mastic gum is also known to have antimicrobial activity against *Helicobacter* pylon, which causes mastic dark gastritis and duodenal ulcer. Parachos S. et al., Antimicrob Agents Cheomother, 51 (2): 551-559, 2007. It has been reported that mastic gum is effective in inhibiting proliferation of causative agents of caries and periodontitis and in reducing plaque on teeth. Takahashi K. et al., J. Periodontol. 74 (4): 501-505, 2003.

Due to its property as a powerful antioxidant and as an excellent natural antibiotics, mastic gum draws attention from cosmetics industry and health food industry. Mastic gum having such various efficacies is composed of a mixture of many high molecular weight organic substances and is water-insoluble (less than 0.01% of solubility). Due to its water-insoulable property, in application, mastic gum is used in a solid state, or dissolved in oil or ethanol. Thus, mastic gum is not practicable for products or liquid products requiring exclusion of oil or ethanol ingredient or especially for hydrates.

The most notable ingredients of mastic gum are mastic oil and triterpenic acids, which involve in its unique functions and efficacies. Triterpenic acids may be masticadienolic acid, isomasticadienoic acid, isomasticadienolic acid, 3-O-acetyl masticadienolic acid, 3-O-acetyl epimasticadienolic acid, 3-O-acetyl isomasticadienolic acid, 3-O-acetyl epi-isomasticadienolic acid, masticadienoic acid, oleanonic acid, moronic acid, etc. The remaining ingredients are natural polymers that help mastic gum maintain its gum shape.

These polymer ingredients are not soluble in purified water at room temperature or at high temperature. Thus, they must be removed by filtration for solubilization of the mastic gum. To make mastic gum applicable in a various industrial fields, it is necessary to develop a method to easily solubilize mastic gum.

Conventional methods of solubilizing mastic gum include (1) solubilizing mastic gum using a centrifugal separator. (2) making mastic gum into liposomes using phospholipid. (3) mixing mastic gum with water and then distilling the mixture to obtain mastic water, etc. Although various technical methods have been proposed for producing a mastic gum solution, e.g., through water dispersion and encapsulation techniques, huddles still remain in solvent treatment or in obtaining a high concentration of mastic gum solution.

Pyridione, Methanol, Ethanol, DMSO, etc. has been known as solvents for aqueous mastic gum solution. Among them, Pyridione, Methanol, DMSO, etc. are harmful to human body. Thus, use of the solvent is not desirable in cosmetic industry or in health food industry. Ethanol is a solubilizing solvent most widely employed for mastic gum. However, utilization of ethanol is also limited for products sensitive to ethanol or in the industry related thereto.

It is desirable that an aqueous mastic gum solution contains no ethanol. To do so, there is a need for developing a method of preparing amastic gum solution which contains a high concentration of mastic gum while containing no ethanol.

Korean Patent Laid-Open No. 10-2018-0055331 discloses a method of: pulverizing mastic gum into fine gum powder using a disk mill; preparing a mixture liquid containing purified water, glycerin, and gums; adding the fine gum powder into the mixture liquid to prepare a mastic-gum-dispersed solution: grinding the mastic-gum-dispersed solution into a nanoparticle solution using a Bead Mill; and filtering the nanoparticle solution using a 50 micrometer fiber filter to produce a mastic gum solution.

The method has a problem as follows. Mastic gum is a water-insoluble substance. While a very small amount of volatile ingredients are dissolved in water, most of ingredients in mastic gum is water-insoluble. Even when the particle size is very small, the amount dissolvable in a mixed solution of water, glycerin and gum is pretty limited. Thus, application of mastic gum solution is limited.

Korean Patent No. 10-131.1011 discloses a process of dissolving mastic gum in an organic solvent such as ether, nucleic acid, acetone, etc. However, this method is problematic in that the final product includes harmful ingredients.

DESCRIPTION OF INVENTION

Problem to be Solved

An objective of the present invention is to provide a mastic gum solution which does not contain an organic solvent such as ethanol. Novel solvent system is employed to solubilize mastic gum which is a water-insoluble substance. Another objective is to provide a mastic gum solution containing a high amount of active ingredients.

Solution to Solve the Problems

In an embodiment of the present invention, provided is a method of solubilizing mastic gum, including: dissolving mastic gum in ethanol to prepare a first solution; mixing polyol and purified water to prepare a second solution; mixing the first solution and the second solution to prepare a third solution; cooling the third solution and filtering out an insoluble polymer resin from the third solution; and removing alcohol from the filtered third solution. The polyol may be glycerin.

The method may further includes: adding a pH adjuster into the second solution. The pH adjuster may include L-Ascorbic acid. The L-ascorbic acid may be 1.5 to 3.0 wt % based on 100 wt % of the third solution.

Advantages of the Invention

According to the present invention as described above, water-insoluble mastic gum can be effectively dissolved to produce an aqueous mastic gum solution in a high concentration. In addition, the aqueous mastic gum solution produced as such is stable to temperature, humidity, sunlight, and other surrounding conditions.

A method according to the present invention simplifies a fabrication process of an aqueous mastic gum solution. It also shortens a process time necessary to produce an aqueous mastic gum solution.

BRIEF DESCRIPTION OF THE DRAWINGS

FIG. 1 is a flowchart showing a method of solubilizing mastic gum according to an embodiment of the present invention.

EMBODIMENTS

Figure 2:
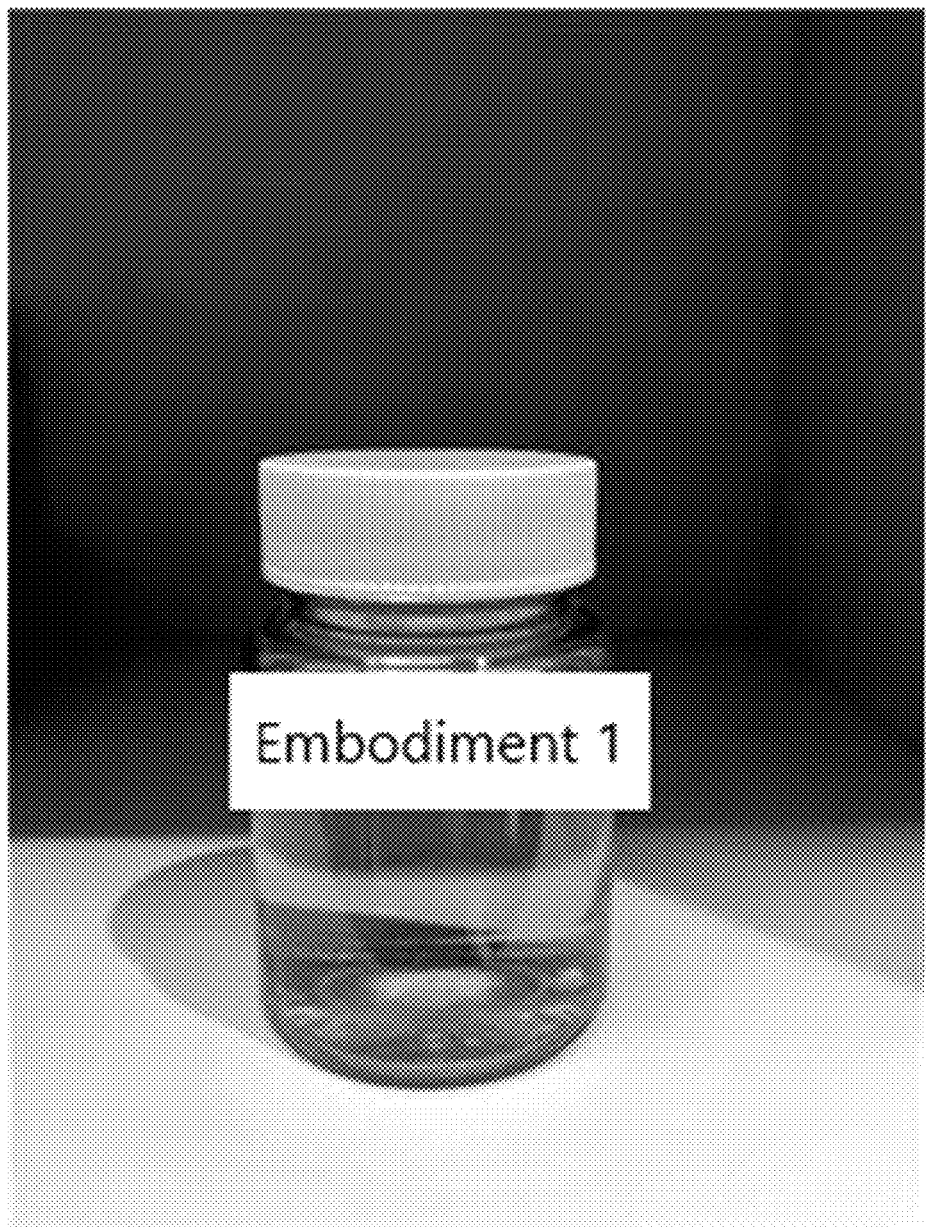
FIGS. 2 to 6 show aqueous mastic gum solutions obtained from Experiments 1-3, respectively.

Hereinafter, the present invention will be described in detail. A method of solubilizing mastic gum according to an embodiment, of the present invention includes: a step (S110) of dissolving mastic gum in ethanol to prepare a first solution; a step (S120) of mixing polyol and purified water to prepare a second solution; a step (S130) of mixing the first solution and the second solution to prepare a third solution; a step (S140) of cooling the third solution and filtering out an insoluble polymer resin from the third solution; and a step (S150) of removing alcohol from the filtered third solution.

In the step (S110) of preparing a first solution, mastic gum is dissolved in alcohol to prepare a mastic gum solution. The alcohol is preferably heated to 50 Celsius degrees (° C.). The content of mastic gum is 0.01 to 40.00 wt % based on 100 wt % of the third solution, and the content of alcohol alcohol is 0.01 to 50.00 wt % based on 100 wt % of the third solution.

In the step (S120) of preparing the second solution, the polyol is added to the purified water, preparing a solubilizing solvent for the mastic gum. The polyol may be monohydric alcohol, dihydric alcohol or trihydric alcohol. Specifically, the polyol may be butylene glycol, dipropylene glycol, propylene glycol or glycerin. More preferably, the polyol is glycerin.

The content of the polyol may be 0.10 to 30.00 wt % based on 100 wt % of the third solution. The second solution may further include a pH adjuster. The pH adjuster may be acidic substance. The pH adjuster may be alpha hydroxy acid (AHA) or vitamin C. Alpha hydroxy acid (AHA) may be citric acid, lactic acid, tartaric acid or malic acid. The vitamin C may be L-Ascorbic acid.

The content of the pH adjuster may be 0.1 to 10.00 wt %, preferably 1.5 to 3.0 wt % based on 100 wt % of the third solution. 100 wt % of the third solution is a sum of the first solution and the second solution.

L-Ascorbic acid softens polymer structure of mastic gum, thereby helping mastic gum easily dissolve in the solvent and stabilizing the mastic gum aqueous solution. Addition of L-Ascorbic acid affects pH of the mastic gum aqueous solution. The amount of L-Ascorbic in the mastic gum aqueous solution is determined in consideration of several factors including the followings.

First, the mastic gum aqueous solution is maintained stable when pH of the mastic gum aqueous solution is 3.00 to 3.50. Second, L-Ascorbic acid is also maintained stable at pH 3.00-3.50. Third, the pH range allowed for a cosmetic composition is 3.00-11.00.

Considering such factors as a whole, it, preferred to control the content of L-Ascorbic acid in the mastic gum aqueous solution to be 1.5-3.0 wt % based on 100 wt % of the mastic gum aqueous solution (i.e., the third solution).

Hereinafter, the present invention will be described in more detail with reference to Examples. These examples are provided merely for illustration purpose. It is apparent to those skilled in the art that the scope of the present invention is not limited thereto. All content (w/w %) presented in the following Examples are measured based on 100 wt % of the third solution. All temperature unit presented in the Examples is Celsius.

Example 1: Formation of Mastic Gum Solution (I)

Ethanol was warmed to 50 Celsius degrees (C). 0.1-25 wt % of mastic gum was slowly added to 50 wt % of the warmed ethanol while the warmed ethanol is stirred using an AGI Mixer, forming a mastic gum-alcohol alcohol solution (the first solution).

10-25 wt % of glycerin and 10-25 wt % of purified water were mixed and warmed up to 65 Celsius degrees (° C.), forming a mixture solution (the second solution).

The first solution was slowly mixed into the second solution while the second solution is stirred using the AGI mixer (500 rpm, 10 min). Then, the mixture solution was cooled down to room temperature. The cooled solution was subject to a first filtration process using a filter paper. Then, fractional distillation was performed to remove ethanol from the resultant solution using a fractional distillation apparatus at 79 Celsius degrees (° C.).

The resultant solution, which was obtained after the fractional distillation, was subject to a second filtration process. The resultant mastic gum solution (I) was sealed and aged at room temperature.

Example 2: Formation of Mastic Gum Solution (II)

A mastic gum solution (II) was prepared by the same process as in Example 1, except for replacing glycerin with butylene glycol to prepare the second solution.

Example 3: Formation of Mastic Gum Solution (II)

A mastic gum solution (III) was prepared by the same process as in Example 1, except for replacing glycerin with dipropylene glycol to prepare the second solution.

The mastic gum solutions (I), (II), and (III) prepared in Examples 1, 2 and 3, respectively, are shown in Table 1.

TABLE 1

| Solution | | Ingredient | Content (wt %) | Note |
|---|---|---|---|---|
| Example 1 | First Solution | mastic gum | 0.10~25.0 wt % | Insoluble substance |
| | | ethanlol | 50.00 wt % | 1$^{st}$ Solvent |
| | Second Solution | glycerin | 10.00~25.00 wt % | Solution Sabilizer |
| | | purified water | 10.00~25.00 wt % | 2$^{nd}$ Solution |
| Example 2 | First Solution | mastic gum | 0.10~25.00 wt % | Insoluble substance |
| | | ethanol | 50.00 wt % | 1$^{st}$ Solvent |
| | Second Solution | butylene glycol | 10.00-25.00 wt % | Solution Stabilizer |
| | | purified water | 10.00~25.00 wt % | 2$^{nd}$ Solution |
| Example 3 | First Solution | mastic gum | 0.10~25.00 wt % | Insoluble substance |
| | | ethanol | 50.00 wt % | 1$^{st}$ Solvent |
| | Second Solution | dipropylene glycol | 10.00~25.00 wt % | Solution Stabilizer |
| | | purified water | 10.00~25.00 wt % | 2$^{nd}$ Solution |

Figure 3:
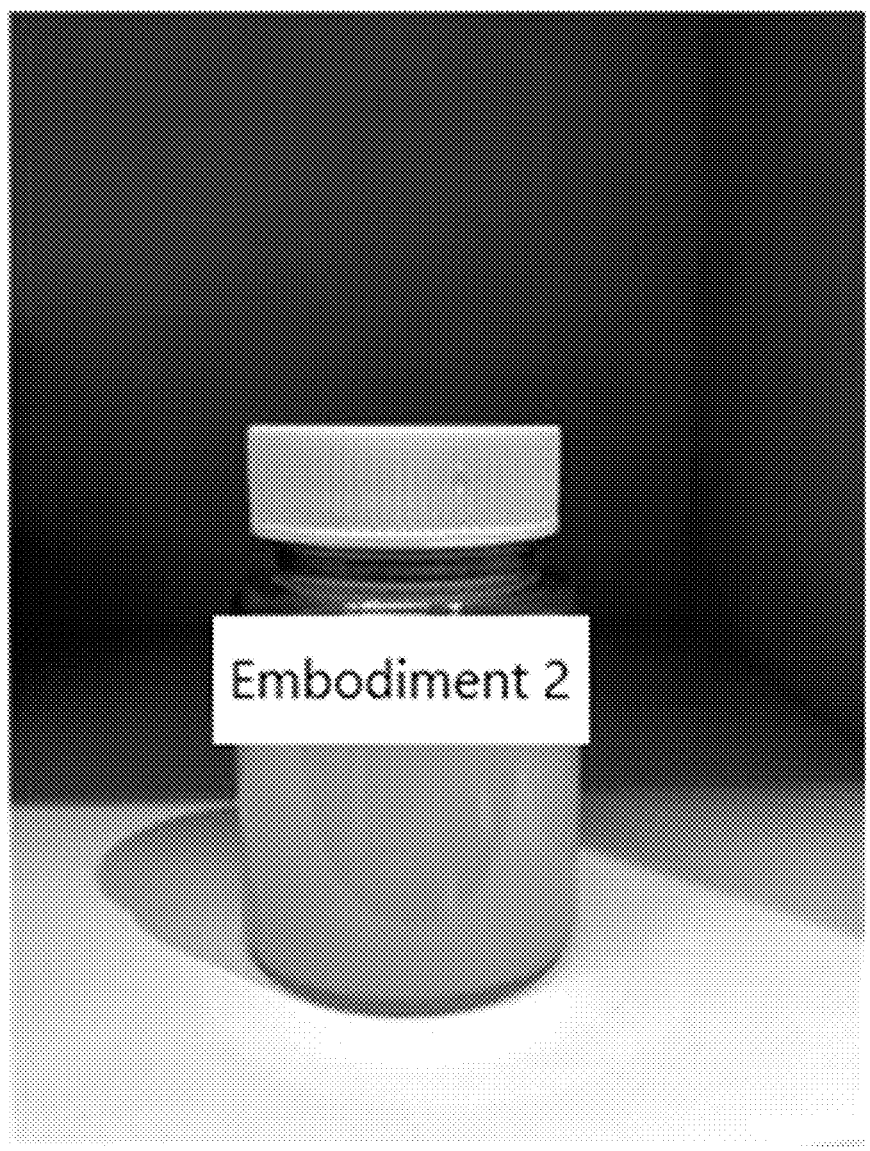
Figure 4:
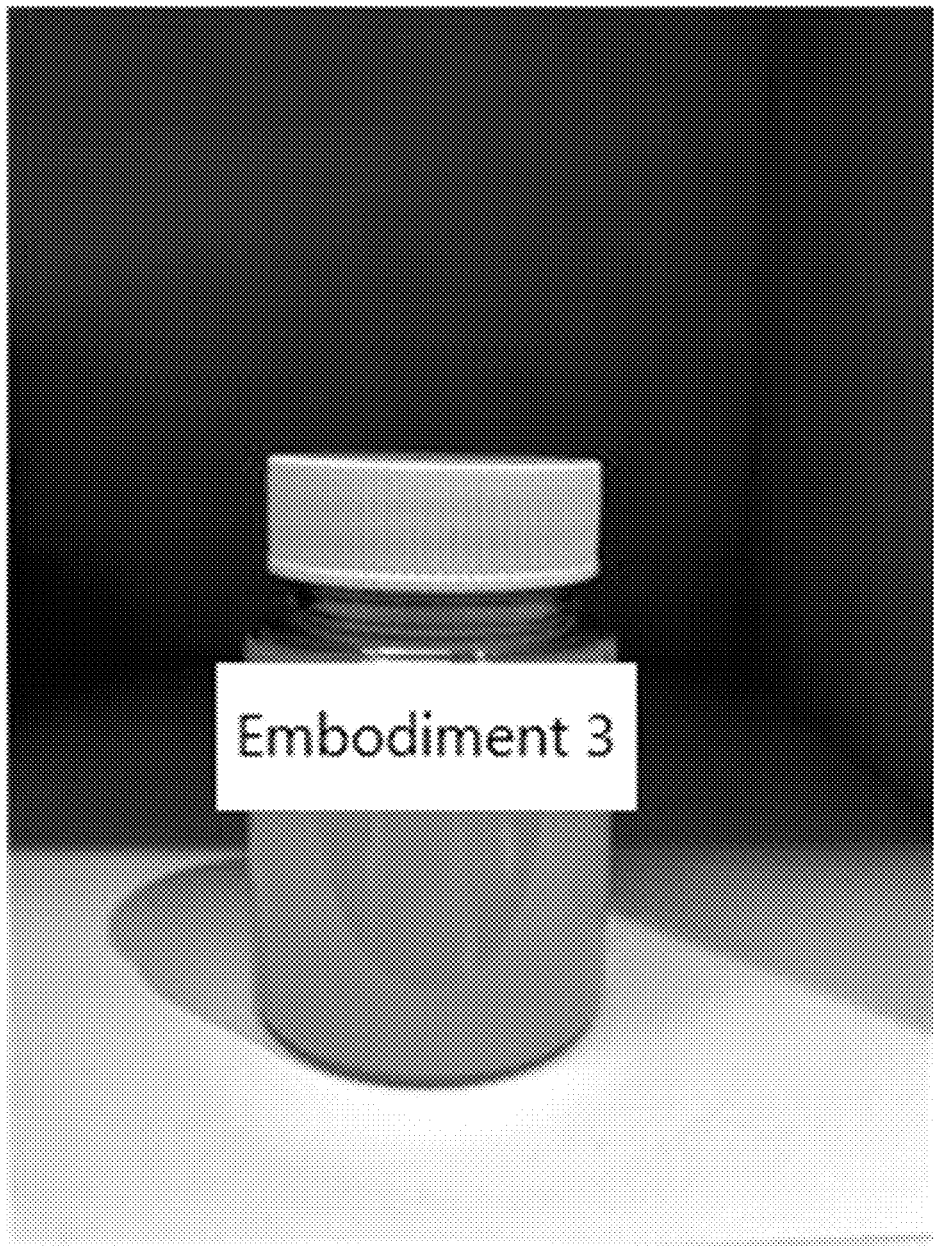

FIGS. 2 to 4 show aqueous mastic gum solution samples obtained from Experiments 1-3, respectively. Referring to 2 to 4 (see FIG. 2 for Example 1; see FIG. 3 for Example 2; see FIG. 4 for Example 3), the Example 1 shown in FIG. 2 was the clearest when observed with naked eyes. From this fact, it is noted that glycerin is more suitable polyol than other polyols in solubilizing mastic gum.

Butylene glycol, dipropylene glycol, and propylene glycol, each of which is bivalent polyol having two —OH groups in unit molecule, was excellent. The solubility of mastic gum was found good in any of these polyols. However, mastic gum showed better solubility in glycerin compared with the other two polyols. This indicates that glycerin better serves as a stabilizer of mastic gum.

In addition, from a practical point of view, an aqueous solution containing polyol such as butylene glycol, dipropylene glycol, and propylene glycol is difficult to be used in the health food or beverage industry. In contrast, glycerin is used as a sweetener in foods. Thus, glycerin is advantageous over other polyols in that it can be applicable in the health food or beverage industry.

Example 4: Mastic Gum Solution (IV) Containing Alpha-Hydroxy Acid (AHA)

Ethanol is warmed to 50 Celsius degrees (° C.). 20 wt % of mastic gum was slowly added to 50 wt % of warm ethanol while the warm ethanol is being stirred using an AGI Mixer, preparing a mastic gum-alcohol solution (a first solution).

14 wt % of glycerin, 3.00 wt % of alpha-hydroxy acid (AHA), and 13 wt % of purified water were mixed together to prepare a second solution. The second solution was warmed up to 65 Celsius degrees (° C.).

While the second solution is being stirred using the AGI mixer (500 rpm, 10 min), the first solution was slowly mixed into the second solution. Then, the mixture solution was cooled down to room temperature. The cooled solution was subject to a first filtration process using a filter paper. Then, fractional distillation was performed to remove ethanol from the resultant solution using a fractional distillation apparatus at 79 Celsius degrees (° C.).

The resultant solution, which was obtained after the fractional distillation, was subject to a second filtration process. The final resultant solution was sealed and aged at room temperature.

Example 5: Mastic Gum Solution (V) Containing L-Ascorbic Acid (Pure Vitamin C)

A mastic gum solution (V) was prepared by the same process as in Example 4, except for (i) replacing 3.00 wt % of alpha-hydroxy acid (AHA) with 2 wt % L-ascorbic acid and (ii) replacing 13 wt % of purified water with 14 wt % of purified water to prepare the second solution.

The mastic gum solutions IV and V prepared in Examples 4 and 5, respectively, are shown in Table 2, below. As mentioned above, all concent (w/w %) presented in Examples 4-5 are measure based on 100 wt % of the third solution. The third solution is a mixture of the first solution and the second solution.

TABLE 2

| | Solution | Ingredient | Content (wt %) | Note |
|---|---|---|---|---|
| Example 4 | First Solution | mastic gum | 20.00 wt % | Insoluble substance |
| | | ethanol | 50.00 wt % | 1$^{st}$ Solvent |
| | Second Solution | glycerin | 14.00 wt % | Solution Stabilizer |
| | | alpha-hydroxy acid (AHA) | 3.00 wt % | pH Adjuster |
| | | purified water | 13.00 wt % | 2$^{nd}$ Solution |
| Example 5 | First Solution | mastic gum | 20.00 wt% | Insoluble substance |
| | | ethanol | 50.00 wt % | 1$^{st}$ Solvent |
| | Second Solution | glycerin | 14.00 wt % | Solution Stabilizer |
| | | L-ascorbic acid | 2.00 wt % | pH Adjuster |
| | | purified water | 14.00 wt % | 2$^{nd}$ Solution |

Figure 5:
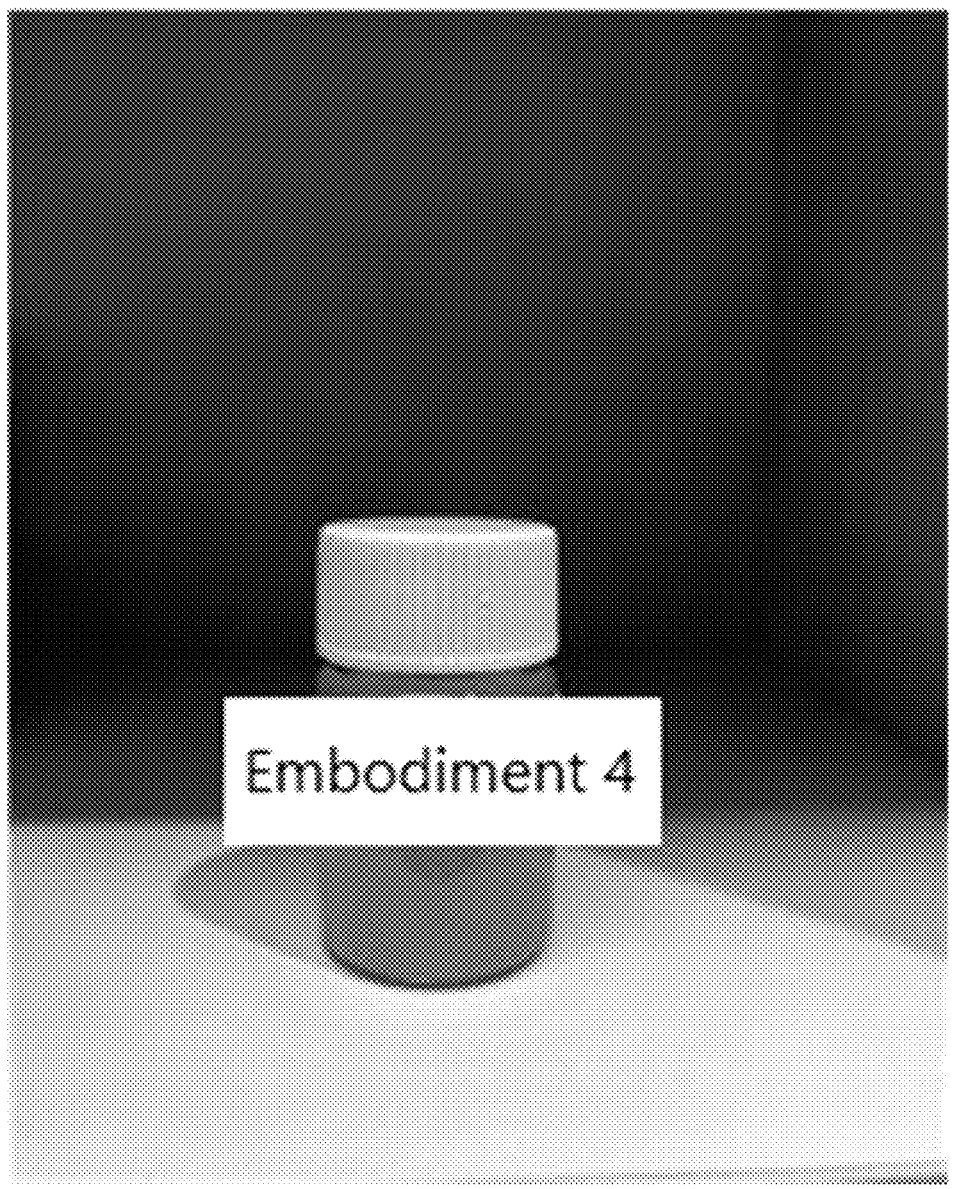
Figure 6:
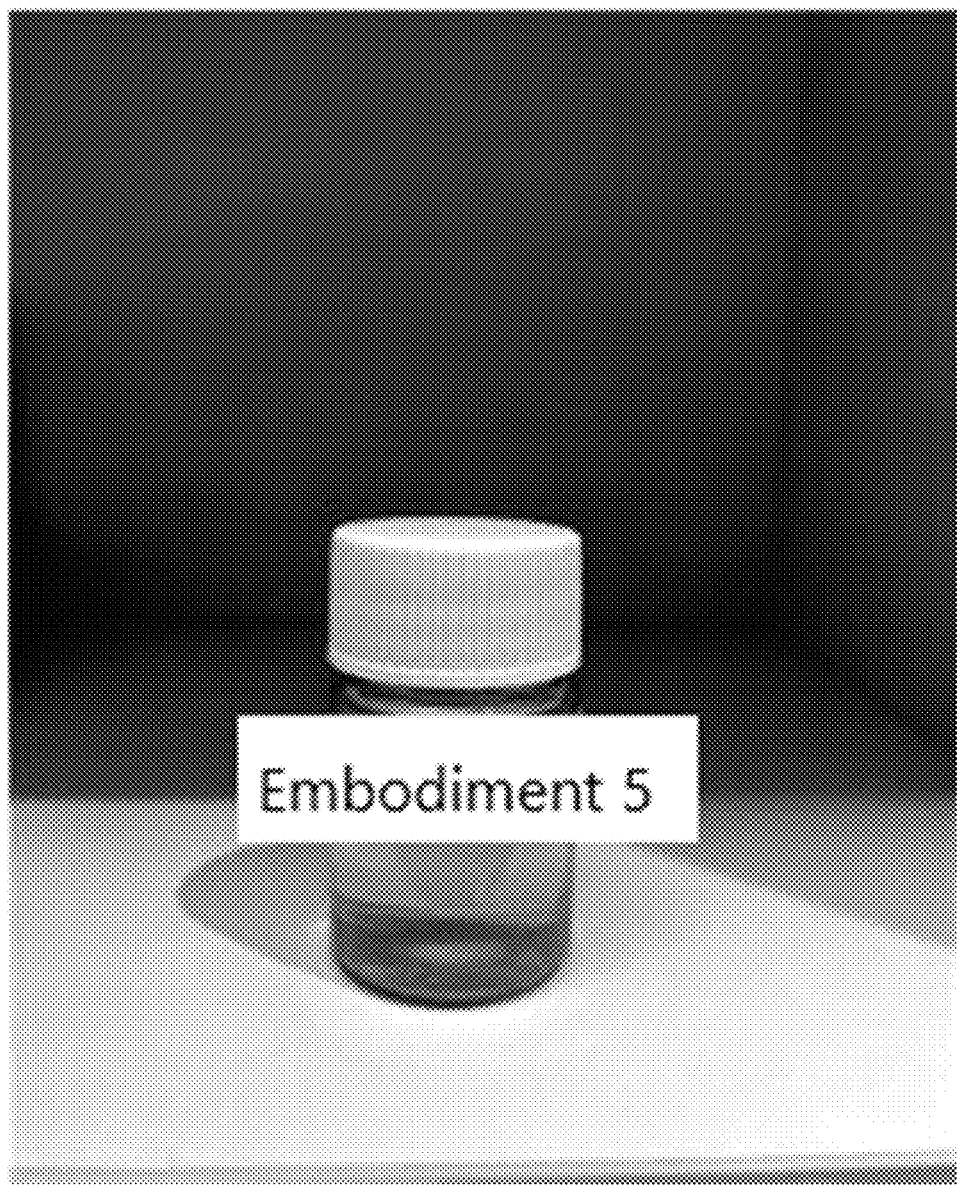

Solubility of mastic gum depending on acid additives was investigated in Examples 4 and 5. The aqueous mastic gum solution prepared in Examples 4 and 5 are shown in FIGS. 5 and 6, respectively.

When an alkali ingredient was added, the aqueous mastic gum solution was unstable with a temperature change. In contrast, when an acidic ingredient was added, the aqueous mastic gum solution showed enhanced stability at a temperature change. Comparing FIGs. with FIG. 6 which are related to Example 4 and Example 5, respectively, the aqueous mastic gum solution obtained in Example 4 was clearer than the aqueous mastic gum solution obtained in Example 5. That is, the aqueous mastic gum solution containing vitamin C (L-ascorbic acid) was found more stable than the aqueous mastic gum solution containing alpha-hydroxy acid (AHA).

This may be because an acidic substance can gently swell polymers contained in mastic gum, helping active ingredients in the mastic gum dissolve into an aqueous solvent.

Example 6: Preparation of Aqueous Mastic Gum Solutions VI-1 to VI-4 Containing L-Ascorbic Acid (Pure Vitamin C)

Aqueous mastic gum solutions VI-1 to VI-4 were prepared by the same process as in Example 5, except for changing ingredient ratios. The composition of the aqueous mastic gum solutions VI-1 to VI-4 as shown in Examples 6-1 through 6-4 in Table 3 below. As mentioned above, all content (w/w %) presented in Examples 6-1 through 6-4 are measured based on 100 wt % of the third solution.

TABLE 3

| | Solution | Ingredient | Content (wt %) | Note |
|---|---|---|---|---|
| Example 6-1 | First Solution | mastic gum | 5 wt % | Insoluble substance |
| | | ethanol | 50 wt % | 1$^{st}$ Solvent |
| | Second Solution | glycerin | 20 wt % | Solution Stabilizer |
| | | L-ascorbic acid | 2 wt % | pH Adjuster |
| | | purified water | 23 wt % | 2$^{nd}$ Solution |

TABLE 3-continued

| Solution | | Ingredient | Content (wt %) | Note |
|---|---|---|---|---|
| Example 6-2 | First Solution | mastic gum | 10 wt % | Insoluble substance |
| | Second Solution | ethanol | 50 wt % | $1^{st}$ Solvent |
| | | glycerin | 20 wt % | Solution Stabilizer |
| | | L-ascorbic acid | 2 wt % | pH Adjuster |
| | | purified water | 18 wt % | $2^{nd}$ Solution |
| Example 6-3 | First Solution | mastic gum | 15 wt % | Insoluble substance |
| | Second Solution | ethanol | 50 wt % | $1^{st}$ Solvent |
| | | glycerin | 15 wt % | Solution Stabilizer |
| | | L-ascorbic acid | 2 wt % | pH Adjuster |
| | | purified water | 18 wt % | $2^{nd}$ Solution |
| Example 6-4 | First Solution | mastic gum | 20 wt % | Insoluble substance |
| | Second Solution | ethanol | 50 wt % | $1^{st}$ Solvent |
| | | glycerin | 15 wt % | Solution Stabilizer |
| | | L-ascorbic acid | 2 wt % | pH Adjuster |
| | | purified water | 13 wt % | $2^{nd}$ Solution |

The solubility of L-ascorbic acid is known about 18 g based on 100 g of water at room temperature. When the content of L-ascorbic acid exceeds 18 g based on 100 g of water, supersaturated L-ascorbic acid precipitates. L-Ascorbic acid is not practical in that it is easily oxidized and broken in room temperature or in water Therefore, considering the amount of purified water included in an aqueous mastic gum solution according to an embodiment of the present invention, a preferable content of L-ascorbic acid is about 1.5 to 3 wt %.

Experimental Example 1: Solubility Analysis

The aqueous mastic gum solutions prepared in the above examples were mixed with purified water, and its solubility was investigated. Other mastic gum solutions, which are prepared from separate experiments, were mixed with purified water, and then their solubility were investigated.

While being stirred, each of the aqueous mastic gum solutions was slowly added into 100 g of purified water. Observed is whether mastic gum dissolved in the respective mastic gum solution would precipitate. The aqueous mastic gum solution was found uniformly dissolved in purified water. When the amount of mastic gum was 0.1 wt % to 1.5 wt %, the aqueous mastic gum solution was found transparent. When the amount of mastic gum was 15 wt % to 50 wt %, the aqueous mastic gum solution was found translucent. When the amount of mastic gum was 70 wt % or more, the aqueous mastic gum solution was found in a light milky color. As mentioned above, the content (w/w %) of mastic gum is measured based on 100 wt % of the aqueous mastic gum solutions.

The aqueous mastic gum solution was stored at room temperature for 7 days and then reinvestigated. Even after a passage of 7 days, no precipitation of mastic gum was observed. This indicates that the aqueous mastic gum solution was well dissolved and stable.

Experimental Example 2: Analysis of Aqueous Mastic Gum Solution

The aqueous mastic gum solution prepared in Example 5 was analyzed using GC-MS Spectroscopy. A silica column (15 mm×0.32 mm R) was used. Helium gas was employed as a carrier gas. Flow rate was set to 1 ml/min at 50 Celsius degrees (C). Pressure was set to 1 psi. An injector and an interface were maintained at 300 Celsius degrees (° C.) and 340 Celsius degrees (° C.), respectively. Oven temperature was raised from 50 Celsius degrees (C) (2 min) to 340 Celsius degrees (° C.) (10 min) at a rate of 10 Celsius degrees (° C.)/min. The analysis result is shown in FIG. 7 and Table 4, below.

TABLE 4

| Peak # | R.Time | I.Time | F.Time | Area | Area % | Height | Heights % | A/H | Chemicals |
|---|---|---|---|---|---|---|---|---|---|
| 7 | 11.095 | 11.070 | 11.165 | 1002214 | 1.67 | 381654 | 1.61 | 2.63 | Cymenol |
| 8 | 11.272 | 11.235 | 11.290 | 1396644 | 2.33 | 698839 | 2.96 | 2.00 | Pinene |
| 8 | 11.272 | 11.235 | 11.290 | 1396641 | 2.33 | 698839 | 2.95 | 2.00 | Myrtenal |
| 17 | 22.369 | 22.230 | 22.305 | 1210847 | 2.02 | 649175 | 2.74 | 1.87 | Cresol |
| 18 | 22.716 | 22.675 | 22.760 | 1471990 | 2.46 | 719932 | 3.03 | 2.04 | Verbenone |
| 18 | 22.716 | 22.675 | 22.760 | 1471990 | 2.46 | 739932 | 3.03 | 2.04 | Camphor |

Figure 7:
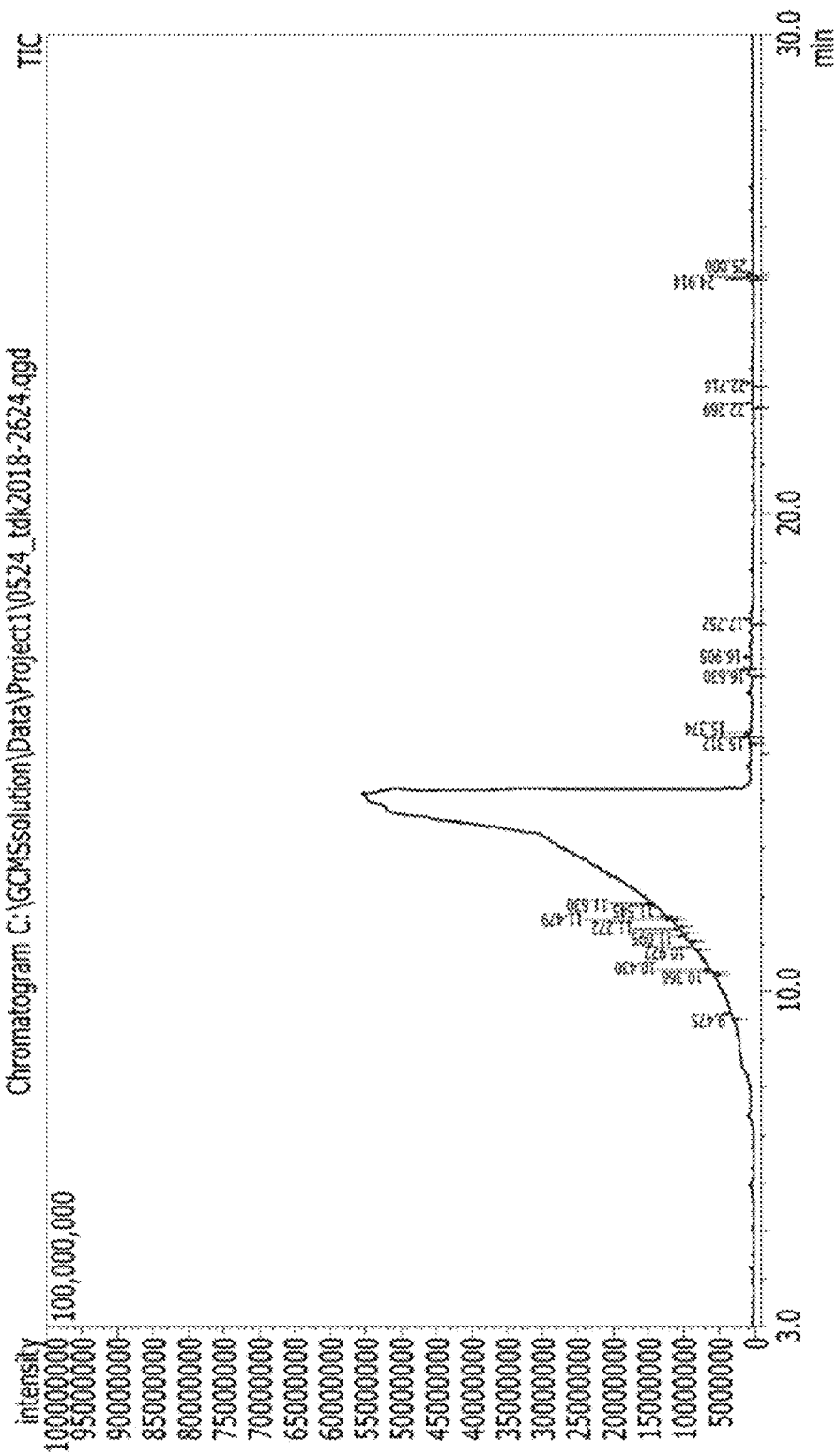
FIG. 7 shows GC-MS spectrum results of an aqueous mastic gum solution obtained according to an embodiment of the present invention.
Figure 8:
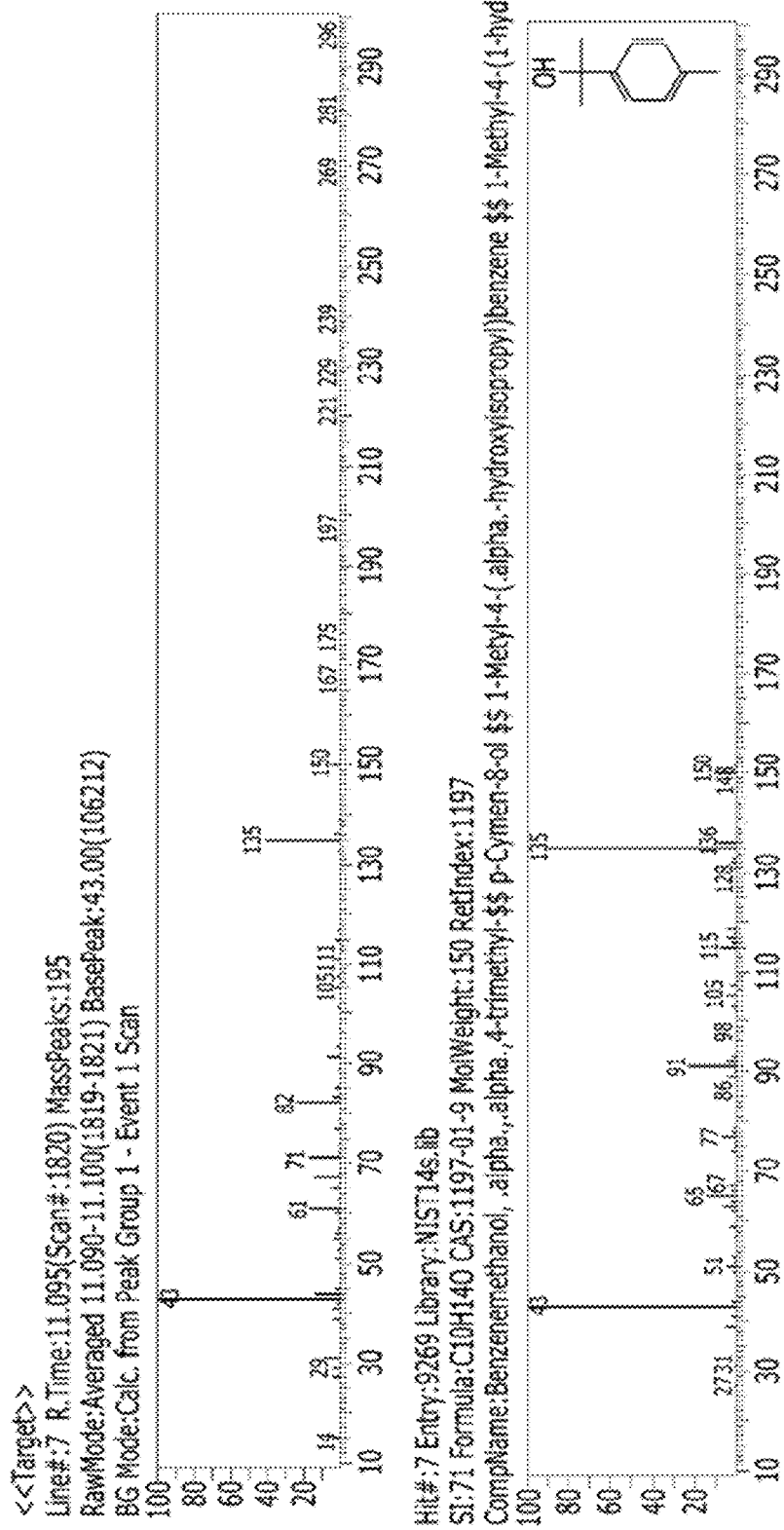
FIGS. 8 to 12 are mass spectrometry showing main ingredients in aqueous mastic gum solutions obtained according to embodiments of the present invention.
Figure 9:
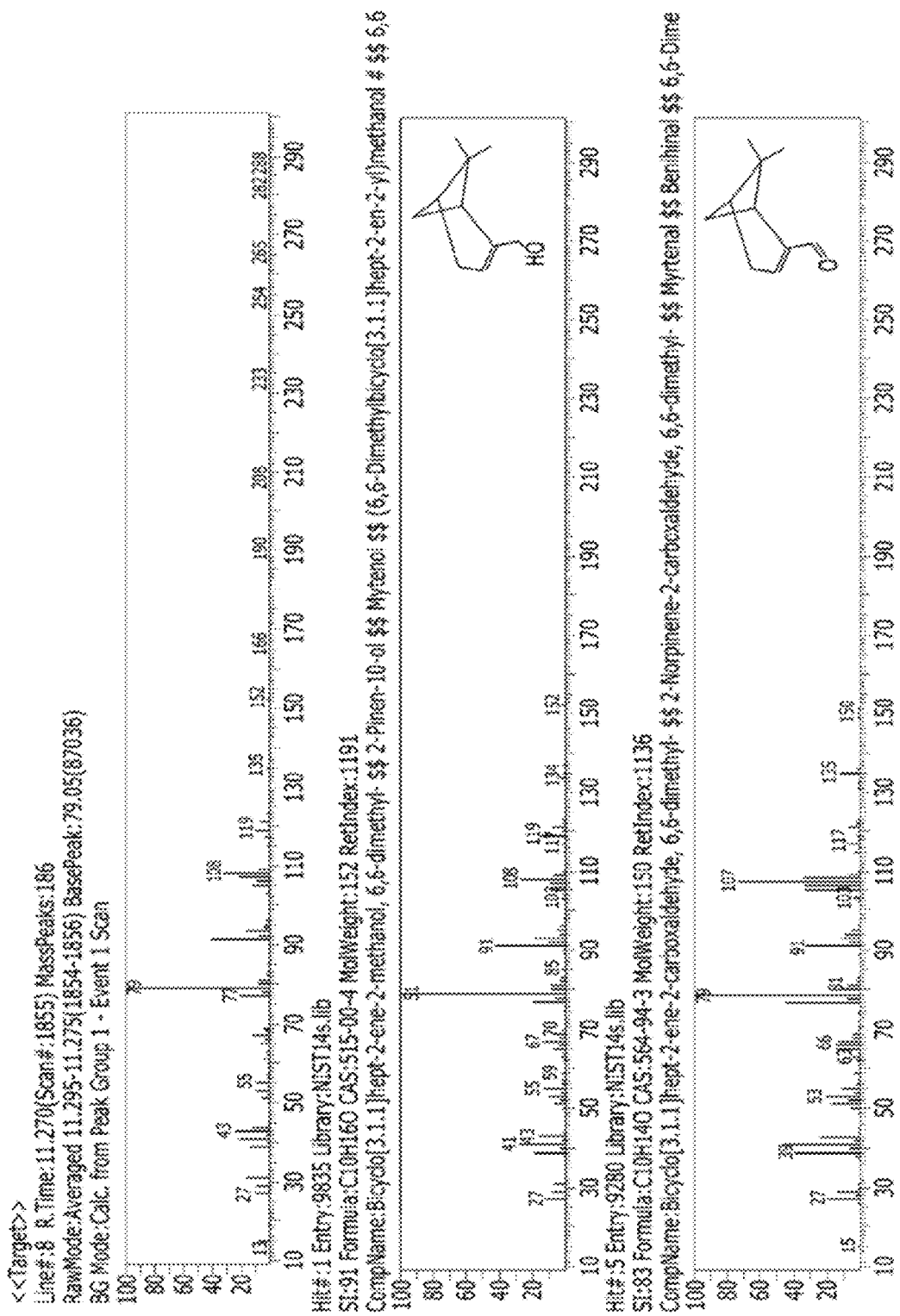
Figure 10:
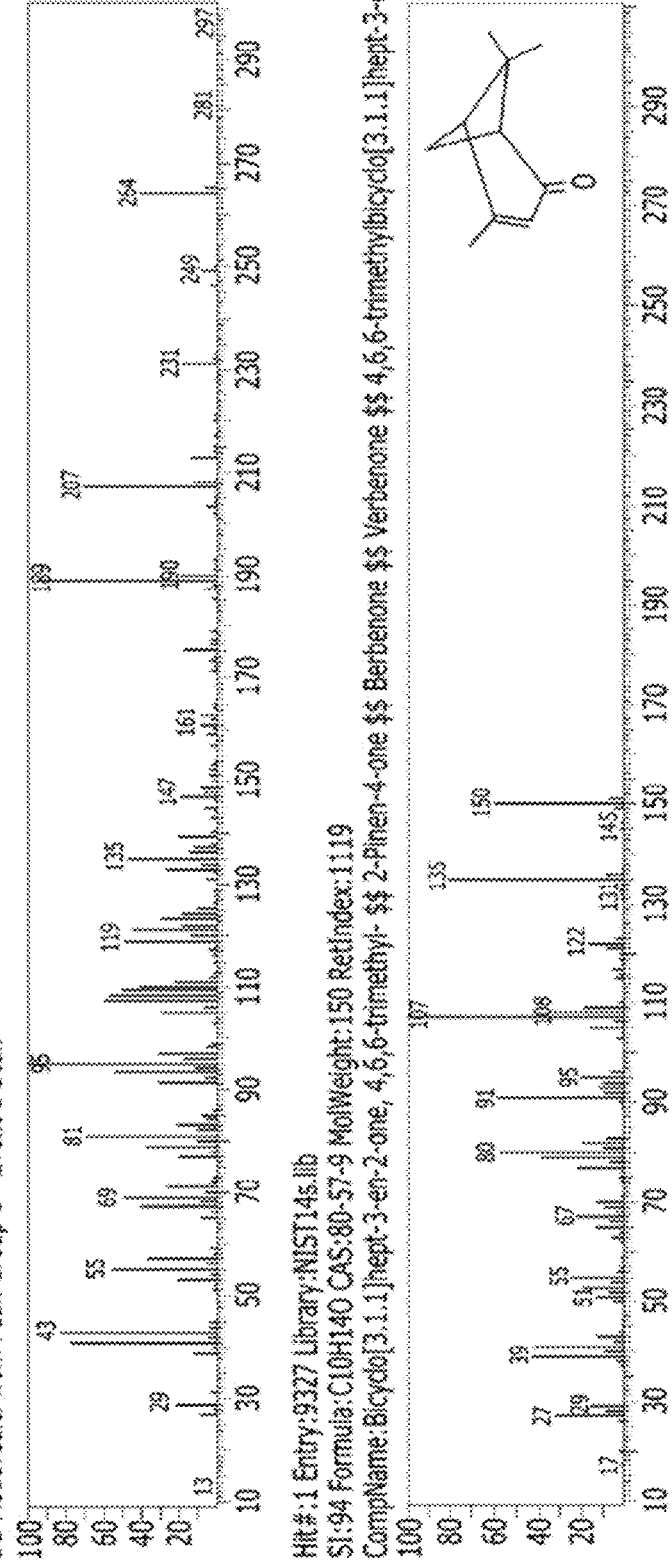
Figure 11:
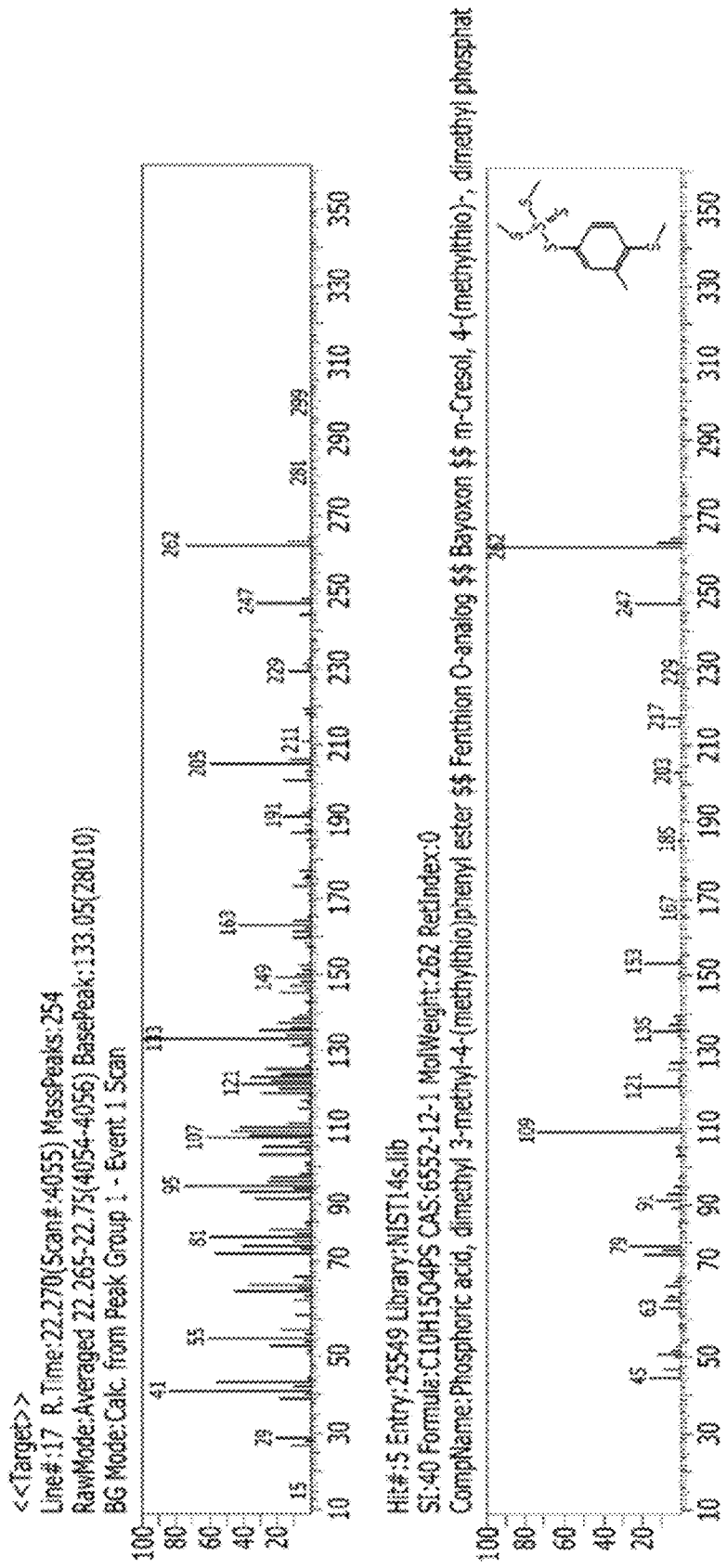
Figure 12:
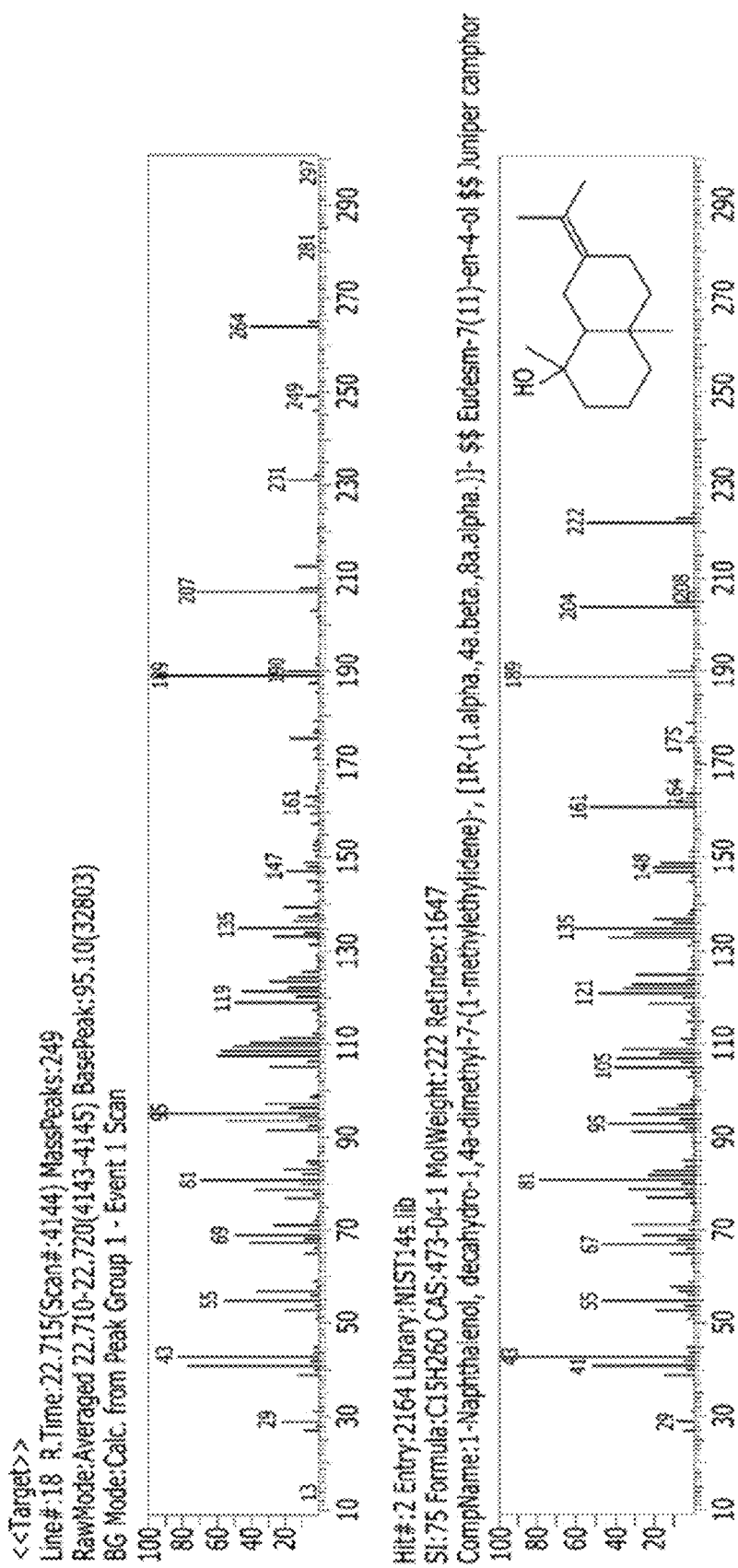

FIG. 7 and Table 4 shows the presence of chemicals such as Cymenol, Pinene (α- & β-), Myrtenal, Cresol, Verbenone, Carveol, Camphor, etc. The chemicals were confirmed by mass spectrometry. FIG. 8 shows mass spectrometry of Cymenol. FIG. 9 shows mass spectrometry of Pinene and Myrtenal. FIG. 10 shows mass spectrometry of Verbenone. FIG. 11 shows mass spectrometry of Cresol. FIG. 12 shows mass spectrometry of Camphor.

Experimental Example 6-1: Skin Composition Containing Aqueous Mastic Gum Solution A skin composition was prepared which contains the aqueous mastic gum solution prepared in Example 5. The skin composition is shown in Table 5, below.

Phase A solution includes purified water, glycerin, xanthan gum, allantoin, EDTA-2Na, panthenol, and a preservative. Phase B solution includes mastic gum (10%) aqueous solution. C phase solution includes 1,3-butylene glycol, Tween 20, and Fragrance. D phase solution includes hyaluronic acid (sodium hyaluronate) and green tea extract (*Camellia sinensis* leaf extract). Phase A. B. C, and D were mixed together, preparing the skin composition.

TABLE 5

| Phase | Ingredient | Content (wt %) |
|---|---|---|
| A | Purified Water | To 100.00 |
| | Glycerin | 10.00 |
| | Xanthan Gum | 0.05 |
| | Allantoin | 0.10 |
| | EDTA-2Na | 0.04 |
| | Panthenol | 0.50 |
| | Preservative | 2.00 |
| B | mastic gum (10%) aqueous solution | 3.00 |
| C | 1,3-Butylene Glycol | 4.00 |
| | Tween 20 | 0.50 |
| | Fragrance | 0.06 |

TABLE 5-continued

| Phase | Ingredient | Content (wt %) |
|---|---|---|
| D | Sodium Hyaluronate | 0.02 |
|  | *Camellia Sinensis* Leaf Extract | 1.00 |

Experimental Example 6-2: Cream Composition Containing Aqueous Mastic Gum Solution A cream composition was prepared which contains the aqueous mastic gum solution prepared in Example 5. The cream composition is shown in Table 6, below. Phase A solution includes purified water, 1,3-butylene glycol, xanthan gum, DPG-2K, beta-glucan, and L-Arginine. Phase B solution includes cetearyl alcohol, stearic acid, beeswax, sunflower oil hazelnut oil, vitamin acetate, (dimethicone glyceryl stearate)/PEG-100 stearate, and polysorbate 60. The phase A solution was heated to 75 Celsius degrees (C). Then, the phase solution was introduced into the A phase solution to emulsify. Then phase C solution (carbomer), serving as a thickener, is added thereto. Fragrance, serving as the phase D solution, is further added thereto. Phase E solution including Mastic gum (20%) aqueous solution, Sodium Hyaluronate, and *centella asiatica* leaf extract, which collectively serve as an additive, are further added thereto, obtaining the cream composition.

TABLE 6

| Phase | Ingredient | Content (wt %) |
|---|---|---|
| A | Purified Water | To 100.00 |
|  | 1,3-Butylene Glycol | 5.00 |
|  | Xanthan Gum | 0.06 |
|  | DPG-2K | 0.10 |
|  | Beta-Glucan | 3.00 |
|  | L-Arginine | 0.20 |
| B | Cetearyl Alcohol | 2.00 |
|  | Stearic Acid | 0.60 |
|  | Bees Wax | 0.80 |
|  | Sunflower Oil | 4.00 |
|  | Hazelnut Oil | 5.00 |
|  | Vitamin E Acetate | 0.25 |
|  | Dimethicone | 0.50 |
|  | Glyceryl Stearate/PEG-100 Stearate | 1.50 |
|  | Polysorbate 60 | 1.00 |
| C | Carbomer | 0.16 |
| D | Fragrance | 0.10 |
| E | Mastic gum (20%) aqueous solution | 10.00 |
|  | Sodium Hyaluronate | 0.02 |
|  | *Centella Asiatics* Leaf Extract | 1.00 |

Experimental Example 6-3: Essence Composition Containing Aqueous Mastic Gum Solution A essence composition was prepared, which contains the aqueous mastic gum solution prepared in Example 5. The essence composition is shown in Table 7, below.

Phase A solution includes: Purified Water, Glycerin, Xanthan Gum, Allantoin, EDTA-2Na, L-Arginine, Beta-Glucan, and Sodium Hyaluronate. Phase B solution includes: Dipropylene Glycol, Mastic Gum (30%) Aqueous Solution, Polysorbate 20, and Fragrance. Phase C solution includes: Carbomer. Phase D solution includes: green tea extract (*Camellia Sinensis* Leaf Extract.), Centella *Asiatica* Leaf Extract, Adenosine, and Hydrolyzed Collagen. The Phase A, B. C, and D were mixed together, preparing an essence composition as shown in Table 7, below.

TABLE 7

| Phase | Ingredient | Content (wt %) |
|---|---|---|
| A | Purified Water | To 100.00 |
|  | Glycerin | 10.00 |
|  | Xamhan Gum | 0.06 |
|  | Allantoin | 0.10 |
|  | EDTA~2Na | 0.04 |
|  | L-Arginine | 0.24 |
|  | Beta-Glucan | 2.00 |
|  | Sodium Hyaluronate (1%) | 0.03 |
| B | Dipropylene Glycol | 5.00 |
|  | Mastic gum (30%) aqueous solution | 15.00 |
|  | Polysorbate 20 | 1.00 |
|  | Fragrance | 0.06 |
| C | Carbomer | 0.24 |
| D | *Camellia Sinensis* Leaf Extract | 1.00 |
|  | *Centella Asiatica* Leaf Extract | 1.00 |
|  | Adenosine | 0.04 |
|  | Hydrolyzed Collagen | 2.00 |

Experimental Example 6-4: Facial Cleanser Composition Containing Aqueous Mastic Gum Solution A facial cleanser composition was prepared which contains the aqueous mastic gum solution prepared in Example 5. The facial cleanser composition is shown in Table 8, below. Phase A solution includes: Purified Water, Glycerin, Allantoin, and EDTA-2Na. Phase B solution includes: ammonium acrloyldimethytaurate/VP Copolymer. Phase C solution includes: Sunflower Seed Oil, Caprylic/Capric Triglycerides, Cetyl Ethylhexanoate, and Fragrance. Phase D solution includes: a mastic gum (20%) aqueous solution. Phase E solution includes: *Centella Asiatica* Leaf Extract, Niacinamide, and *Eucalyptus* Extract. The Phase A, B, C, D and E were mixed together, preparing the facial cleanser composition shown in Table 8.

TABLE 8

| Phase | Ingredient | Content (wt %) |
|---|---|---|
| A | Purified Water | To 100.00 |
|  | Glycerin | 5.00 |
|  | Allantoin | 0.10 |
|  | EDTA-2Na | 0.04 |
| B | Ammonium Acryloydimethyltaurate/ VP Copolymer | 1.60 |
| C | Sunflower Oil | 4.00 |
|  | Caprylic/Capric Triglycerides | 3.00 |
|  | Cetyl Ethylhexanoate | 1.00 |
|  | Fragrance | 0.10 |
| D | Mastic Gum (20%) Aqueous Solution | 1.00 |
| E | *Centella Asiatica* Leaf Extract | 0.50 |
|  | Niacinamide | 0.50 |
|  | Eucalyptus Extract | 1.00 |

Experimental Example 6-5: Body Lotion Composition Containing Aqueous Mastic Gum Solution A body lotion composition was prepared which contains the aqueous mastic gum solution prepared in Example 5. The body lotion composition is shown in Table 9, below. Phase A solution includes: Purified Water (Glycerin), Glycerin. Xanthan Gum, Allantoin, EDTA-2Na, L-Arginine, Panthenol, Betaine, and Sorbitol. Phase B solution includes: Cetearyl Alcohol, Stearic Acid. Caprylic/Capric Triglycerides. Mineral oil, Olive Oil, Vitamin E Acetate, Glyceryl Stearate/PEG-100 Stearate, and Polysorbate 60. Phase C solution is Carbomer. Phase D solution is Fragrance. Phase E solution includes: Mastic Gum (30%) aqueous solution, Hydrolyzed Collagen, *Portulaca Oleracea* Extract, Betaine, and Green Tea Extract (*Camellia Sinensis* Leaf extract). The Phase A, B, C, D and E solutions were mixed together to prepare the body lotion composition as shown in Table 9.

TABLE 9

| Phase | Ingredient | Content (wt %) |
|---|---|---|
| A | Purified Water | To 100.00 |
|   | Glycerin | 5.00 |
|   | Xanthan Gum | 0.06 |
|   | Allantoin | 0.10 |
|   | EDTA-2Na | 0.04 |
|   | L-Arginine | 0.10 |
|   | Panthenol | 0.50 |
|   | Betaine | 2.00 |
|   | Sorbitol | 1.00 |
| B | Cetearyl Alcohol | 1.20 |
|   | Stearic Acid | 0.50 |
|   | Caprylic/Capric Triglycerdes | 2.00 |
|   | Mineral Oil | 5.00 |
|   | Olive Oil | 2.00 |
|   | Vitamin E Acetate | 0.15 |
|   | Glyceryl Stearate/PEG-100 Stearate | 1.50 |
|   | Polysorbate 60 | 0.80 |
| C | Carbomer | 0.10 |
| D | Fragrance | 0.10 |
| E | Mastic Gum (30%) Soluble Mixture | 1.00 |
|   | Hydrolyzed Collagen | 2.00 |
|   | *Portulaca Oleracea* Extract | 0.50 |
|   | Betaine | 1.00 |
|   | *Camellia Sinensis* Leaf Extract | 0.50 |

Experimental Example 6-6: Mask Sheet Liquid Composition Containing Aqueous Mastic Gum Solution A mask sheet liquid composition was prepared which contains the aqueous mastic gum solution prepared in Example 5. The mask sheet liquid composition is shown in Table 10, below. Phase solution includes: Purified Water, Glycerin Diglycerin, Xanthan Gum, Allantoin, EDTA-2Na, Betaine and Mastic Gum (40%) Aqueous Solution. Phase B solution includes: Dipropylene Glycol, Polysorbate 20, and Fragrance. The Phase A and B solutions were mixed together to prepare the mask sheet liquid composition shown in Table 10, below.

TABLE 10

| Phase | Ingredient | Content (wt %) |
|---|---|---|
| A | Purified Water | To 100.00 |
|   | Glycerin | 5.00 |
|   | Diglycerin | 0.50 |
|   | Xanthan Gum | 0.06 |
|   | Allantoin | 0.10 |
|   | EDTA-2Na | 0.03 |
|   | Betaine | 1.00 |
|   | Mastic Gum (40%) Aqueous Solution | 1.00 |
| B | Dipropylene Glycol | 3.00 |
|   | Polysorbate 20 | 0.50 |
|   | Fragrance | 0.03 |

Embodiments are presented in the present invention. It should be noted that such embodiments are mere examples to help understanding of the present invention and does not limit the scope of the present invention. The scope of the present invention should be construed and defined by the appended claims and their equivalents.

What is claimed is:

1. A method of manufacturing a water-solubilized solution of mastic gum, comprising:
    dissolving mastic gum in ethanol to prepare a first solution;
    mixing polyol and purified water to prepare a second solution;
    mixing the first solution and the second solution to prepare a third solution;
    cooling down the third solution and filtering the third solution to remove insoluble polymer resin; and
    removing alcohol from the filtered third solution.

2. The method of claim 1, wherein the polyol comprises glycerin.

3. The method of claim 1, further comprising adding a pH adjuster into the second solution.

4. The method of claim 3, wherein the pH adjuster comprises L-ascorbic acid.

5. The method of claim 4, wherein a content of the L-ascorbic acid is 1.5 wt % to 3.0 wt %, based on 100 wt % of the third solution.

* * * * *